United States Patent [19]

Lacefield et al.

[11] 4,277,471

[45] Jul. 7, 1981

[54] 1,1-BIPHENYL-2-YL ALKYLAMINES, FORMULATIONS AND ANTIARRHYTHMIC TREATMENT

[75] Inventors: William B. Lacefield, Indianapolis; Richard L. Simon, Greenwood, both of Ind.

[73] Assignee: Eli Lilly and Company, Indianapolis, Ind.

[21] Appl. No.: 123,855

[22] Filed: Feb. 22, 1980

Related U.S. Application Data

[63] Continuation-in-part of Ser. No. 19,534, Mar. 12, 1979, abandoned.

[51] Int. Cl.³ ............... A61K 31/135; A61K 31/275; A61K 31/535; C07C 87/28
[52] U.S. Cl. ................... 424/248.4; 560/38; 560/39; 260/326.43; 562/443; 562/444; 260/326.5 R; 564/164; 564/165; 260/326.62; 564/285; 564/355; 260/326.8; 260/465 E; 260/501.11; 260/501.13; 260/501.15; 260/501.18; 424/248.53; 424/248.54; 424/248.55; 424/248.57; 424/267; 424/274; 424/304; 424/309; 424/316; 424/319; 424/324; 424/329; 424/330; 544/106; 544/163; 544/168; 544/170; 544/171; 544/178; 546/192; 546/230; 546/234; 546/239

[58] Field of Search .......... 260/465 E, 558 A, 559 D, 260/567.6 M, 570.6, 570.8 R, 326.43, 326.5 R, 501.18; 424/304, 324, 329, 330, 248.4, 267, 274, 316, 319; 544/178; 546/230; 560/39, 38; 562/443, 444

[56] References Cited

U.S. PATENT DOCUMENTS

| 4,001,328 | 1/1977 | Molloy | 260/567.6 M |
| 4,055,664 | 10/1977 | Skibbe | 424/330 |
| 4,098,890 | 7/1978 | Molloy | 424/248.4 |
| 4,110,447 | 8/1978 | Gante et al. | 260/570.6 X |

OTHER PUBLICATIONS

Kniffen et al., *The Journal of Pharmacology and Experimental Therapeutics*, vol. 196, pp. 420-432 (1976).
Adelstein et al., Annual Reports in Medicinal Chemistry, vol. 9, p. 67 (1974).

*Primary Examiner*—Dolph H. Torrence
*Attorney, Agent, or Firm*—Charles W. Ashbrook; Arthur R. Whale

[57] ABSTRACT

Biphenylylalkylamines which have anti-arrhythmic activity have been prepared. Pharmaceutical formulations containing such compounds and a method of treating cardiac arrhythmias are provided.

45 Claims, No Drawings

1,1-BIPHENYL-2-YL ALKYLAMINES, FORMULATIONS AND ANTIARRHYTHMIC TREATMENT

CROSS REFERENCE TO RELATED CASES

This is a continuation-in-part of Ser. No. 19,534, filed Mar. 12, 1979, abandoned.

BACKGROUND OF THE INVENTION

Cardiovascular disorders are responsible for thousands of deaths each year. Cardiac arrhythmias are one of these disorders contributing to such deaths. While the true causes of arrhythmias are unknown, it is believed that they are caused by some abnormality in the rate, regularity or site of origin of cardiac impulses, or by disturbances which affect the sequence of activation of the atria and ventricles.

Several drugs currently are used in the treatment of arrhythmias, the most notable including quinidine, procainamide, lidocaine and digitalis. A great deal of interest recently has been generated over a new antiarrhythmic agent, aprindine, a 2-aminoindane derivative; see U.S. Pat. No. 3,923,813. Several diphenylalkylamines also have recently been reported to have useful antiarrhythmic activity; see U.S. Pat. Nos. 4,001,328, 4,034,011 and 3,987,201. Phenoxyalkylamine antiarrhythmic agents also are known; U.S. Pat. No. 3,932,664.

Biphenylyl alkylamines having antiarrhythmic activity are heretofore unknown. It accordingly is an object of this invention to provide such compounds, as well as formulations and a method of treating cardiac arrhythmias.

SUMMARY OF THE INVENTION

This invention concerns biphenyl substituted propyl, butyl, and pentylamines which have antiarrhythmic activity. The invention is particularly directed to compounds defined by the formula

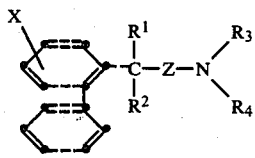

wherein:
X is hydrogen or halo;
$R^1$ is hydrogen, hydroxy, C≡N, $CONH_2$ or $COOR^5$, where $R^5$ is hydrogen or lower alkyl;
$R^2$ is hydrogen or $C_1$—$C_3$ alkyl;
Z is —$(CH_2)_n$—, or

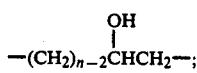

n is 2, 3 or 4;
$R^3$ and $R^4$ independently are hydrogen, lower alkyl, lower alkenyl, phenyl alkyl, or taken together with the nitrogen to which they are attached form a cyclic ring selected from pyrrolidino, piperidino and morpholino; and the pharmaceutically acceptable acid addition salts and quaternary ammonium salts thereof.

Preferred compounds have the above formula wherein X is hydrogen, 5-fluoro, 5-chloro or 5-bromo; $R^1$ is hydrogen, hydroxy, C≡N, $CONH_2$ or COOH; $R^2$ is hydrogen or methyl; Z is —$CH_2CH_2$—, —$CH_2CH_2CH_2$— or

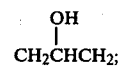

with the limitation that when Z is

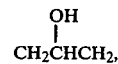

$R^1$ is hydrogen; $R^3$ and $R^4$ are as defined above; and the pharmaceutically acceptable salts thereof.

Additionally preferred compounds have the above formula wherein one or more of the following definitions apply:
1. X is hydrogen or fluoro;
2. $R^1$ is hydroxy;
3. $R^1$ is C≡N;
4. $R^1$ is $CONH_2$;
5. $R^2$ is hydrogen;
6. $R^3$ is other than hydrogen;
7. $R^3$ is $C_1$-$C_4$ alkyl, most preferably isopropyl;
8. $R^4$ is hydrogen or $C_1$-$C_4$ alkyl;
9. Z is —$CH_2CH_2CH_2$—;
10. Z is

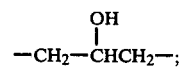

11. the pharmaceutically acceptable acid addition salt;
12. the pharmaceutically acceptable quaternary ammonium salt.

This invention also provides pharmaceutical formulations useful in the treatment of cardiac arrhythmia comprising an antiarrhythmic amount of a compound defined by the above formula in combination with a suitable carrier therefor.

An additional embodiment of this invention is a method of treating cardiac arrhythmia comprising administering to a subject suffering from an arrhythmia and in need of treatment or to a subject suspected of developing an arrhythmia an antiarrhythmically effective dose of a biphenylyl alkylamine having the above general formula.

DETAILED DESCRIPTION OF THE INVENTION

Throughout this specification and in the appended claims, "lower alkyl" includes $C_1$—$C_6$ alkyl groups such as methyl, ethyl, n-propyl, isopropyl, n-butyl, tert-butyl, n-pentyl, isopentyl, n-hexyl, 2-methylpentyl, 2,3-dimethylbutyl and the like. "Lower alkenyl" is used to designate groups of the formula $CH_2$ $C_2$-$C_5$ alkenyl, such as allyl, 2-pentenyl, 2-methyl-2-pentenyl, 3-hexenyl, 4-methyl-2-pentenyl, and related alkenyl groups. "Phenyl alkyl" refers to phenyl-$C_1$-$C_3$ alkyl groups such as benzyl, 2-phenethyl and 3-phenylpropyl. "Halo" includes fluoro, chloro, bromo and iodo.

The biphenylyl alkylamines provided by the invention are basic substances which readily react with organic and inorganic acids to form salts. Those acid addition salts which are substantially as non-toxic as the free amine from which they are derived are "pharmaceutically acceptable acid addition salts" and are provided as a further embodiment of the invention. Such salts are those prepared with common inorganic acids such as hydrochloric acid, hydrobromic acid, sulfuric acid, phosphoric acid, perchloric acid and the like. Pharmaceutically acceptable acid addition salts also are prepared by reaction of the amines with organic acids such as formic acid, acetic acid, succinic acid, maleic acid, para-toluenesulfonic acid, methanesulfonic acid, citric acid and the like.

The invention additionally contemplates quaternary ammonium salts of amine bases of the above formula, which are also pharmaceutically acceptable salts. Such salts are prepared by reaction of a biphenylyl alkyl tertiary amine of the invention with an alkylating agent such as a $C_1$–$C_6$ alkyl halide, $C_1$–$C_6$ alkyl sulfate, $C_1$–$C_6$ alkyl benzene sulfate and the like. Typical alkylating agents commonly used to form acceptable quaternary ammonium salts include methyl bromide, n-butyl iodide, isopentyl chloride, dimethylsulfate, ethyl benzenesulfate, diisopropylsulfate and the like.

The biphenylyl alkanolamines provided by this invention, compounds having the above general formula wherein $R^1$ is hydroxy and Z is —$(CH_2)_n$—, can be prepared directly by reaction of a biphenyl aldehyde or a biphenyl $C_1$–$C_3$ alkyl ketone with an aminoalkyl Grignard reagent. Such reaction is depicted by the following scheme:

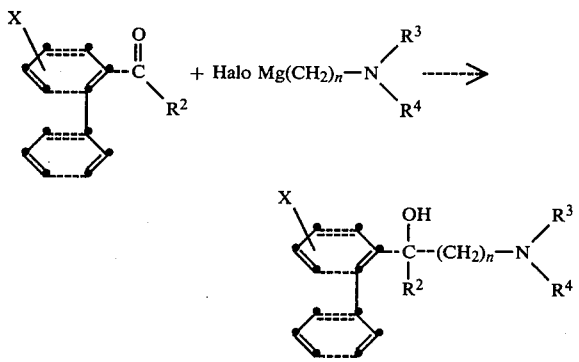

wherein X, $R^2$, $R^3$ and $R^4$ are as defined above and n is 2, 3 or 4. The reaction is carried out by combining approximately equimolar quantities of the biphenyl aldehyde or biphenyl alkyl ketone with an appropriately substituted aminoethyl, aminopropyl or aminobutyl magnesium halide in an unreactive organic solvent such as diethyl ether or tetrahydrofuran. When the reaction is carried out at reflux temperature, it normally is substantially complete within about four to about eight hours. The product is then readily isolated by simply diluting the reaction mixture with aqueous ammonium chloride, separating the organic layer, and removing the solvent, for instance by evaporation under reduced pressure. The product can be purified if desired by standard procedures such as distillation, crystallization, salt formation or the like.

An alternative and preferred process for preparing the biphenylyl butanol and pentanolamines of this invention, compounds of the above general formula wherein $R^1$ is hydroxy and Z is —$CH_2CH_2CH_2$— or —$CH_2CH_2CH_2CH_2$—, comprises reacting a biphenyl aldehyde or biphenyl alkyl ketone with a suitably N-substituted 3-aminoalkynyl carbanion to form the corresponding biphenylyl alkynylamine, followed by exhaustive reduction to provide the compound of the invention. Such process is depicted as follows:

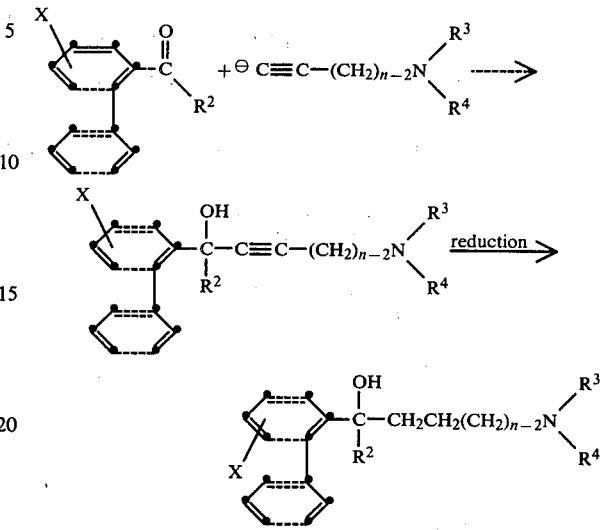

wherein X, $R^2$, $R^3$, $R^4$ and n have the above-defined meanings. The process is carried out by first reacting about equimolar quantities of a biphenyl aldehyde or biphenyl alkyl ketone with an aminoalkynyl carbanion formed by reaction of the corresponding ω-aminoalkyne with a strong base. Strong bases commonly employed to form the alkynyl carbanion include methyl lithium, butyl lithium, methyl or ethyl magnesium bromide, triphenylmethyl sodium and the like. The biphenyl aldehyde or ketone generally is mixed with the aminoalkyne and strong base in an unreactive organic solvent such as diethyl ether or tetrahydrofuran, typically at a reduced temperature of about −80° to about −50° C. The alkynyl carbanion is formed in situ and then reacts with the aldehyde or ketone. The reaction mixture typically is stirred at a reduced temperature for about one hour, and then is heated to reflux and stirred for an additional eight to ten hours. The intermediate biphenylyl alkynylamine which is formed can be isolated by diluting the reaction mixture with water, thereby decomposing any unreacted carbanion, and then separating the organic layer and removing the solvent therefrom. If desired, the intermediate can be further purified by standard procedures, including acid and base extraction.

The biphenylyl alkynylamine next is reduced to yield the corresponding biphenylyl alkylamine of the invention. Such exhaustive reduction typically is carried out by hydrogenation in the presence of a catalyst such as palladium or platinum. For example, a biphenylyl butynylamine such as N-isopentyl-4-hydroxy-4-(1,1'-biphenyl-2-yl)-2-butynylamine is dissolved in a suitable organic solvent such as methanol or ethanol and stirred for about two to four hours at about 20 to about 50° C. under a hydrogen atmosphere of about 20 to about 80 psi, in the presence of a hydrogenation catalyst such as palladium suspended on carbon. The reduced product, for instance N-isopentyl-4-hydroxy-4-(1,1'-biphenyl-2-yl)butylamine, is isolated by filtering the reaction mixture to remove the catalyst and then evaporating the reaction solvent from the filtrate. The amine thus formed can be further purified if desired by standard methods such as acid and base extraction, crystallization from solvents such as diethyl ether or Skelly-B, salt formation, chromatography and the like.

The above-described process is a preferred method for preparing the 4-hydroxy-4-(1,1'-biphenyl-2-yl)butylamines and the 5-hydroxy-5-(1,1'-biphenyl-2-yl)pentylamines of the invention. A preferred method for preparing the 3-hydroxy-3-(1,1'-biphenyl-2-yl)propylamines embraced by the invention comprises reacting a biphenyl $C_1$–$C_3$ alkyl ketone with an amine in the presence of formaldehyde according to Mannich reaction conditions to afford a 3-oxo-3-biphenylyl-propylamine, followed by reduction of the oxo group. For example, a biphenyl methyl ketone such as 2-acetyl-5-fluoro-1,1'-biphenyl can be reacted with an excess of formaldehyde and an amine of the formula $HNR^3R^4$ in a suitable solvent such as ethanol. The formaldehyde typically is introduced as an aqueous solution of formaldehyde, or as the solid trimer (i.e. trioxymethylene) or as the solid polymer (i.e. polyoxymethylene). The reaction usually is carried out employing a secondary amine such as dimethylamine, methyl ethylamine, diisopropylamine, methyl benzylamine, pyrrolidine, piperidine and the like, thereby avoiding any undesired side reactions which might occur in the presence of a primary amine or ammonia. The reaction normally is conducted at reflux temperature, and routinely is complete within about six to twelve hours. The product, a 3-oxo-3-biphenylylpropylamine, is isolated by evaporation of the reaction solvent, followed by crystallization of the amine, generally as an acid addition salt. The 3-oxo-3-biphenylylpropylamine thus formed next is reduced by reaction with any of a number of reducing agents, including sodium borohydride, catalytic hydrogenation and the like.

The biphenylyl aminoalkyl nitriles of this invention, compounds defined by the above general formula wherein $R^1$ is $C\equiv N$, are prepared by alkylating a 1,1'-biphenyl-2-yl-acetonitrile with an aminoalkyl alkylating agent. The reaction is depicted below:

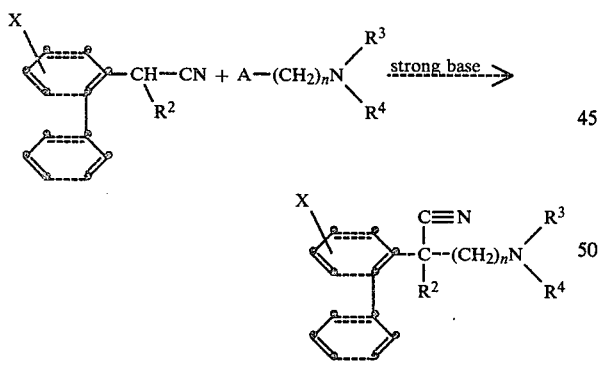

in which X, $R^2$, $R^3$ and $R^4$ are as defined above, n is 2, 3 or 4 and A is a leaving group such as chloro, bromo, iodo, azido, para-toluenesulfonyl, methanesulfonyl and the like. The alkylation is accomplished by first reacting the biphenylyl acetonitrile with a strong base such as sodium or potassium amide, potassium tert-butoxide, sodium dimsyl, lithium diisopropylamide, or the like, in an unreactive organic solvent such as toluene, benzene, diethyl ether, xylene, or tetrahydrofuran. The strong base reacts with the biphenylyl acetonitrile to form a reactive carbanion which, upon addition of the aminoalkyl alkylating agent to the reaction mixture, displaces the leaving group of the alkylating agent and provides a compound of this invention. The alkylation reaction typically is complete within about eight to sixteen hours when carried out at a temperature of about 30° to about 150° C., typically at reflux temperature. The product, a 3-cyano-3-biphenylylpropylamine, a 4-cyano-4-biphenylylbutylamine or a 5-cyano-5-biphenylylpentylamine, is isolated by simply diluting the reaction mixture with water and extracting the product into a suitable solvent such as benzene or diethyl ether. Evaporation of the solvent from the extracts then provides the product, which can be further purified if desired by routine methods.

The biphenylyl aminoalkyl nitriles thus formed are valuable not only as antiarrhythmic agents, but additionally serve as intermediates leading to other compounds of this invention. For example, acid hydrolysis of a biphenylyl aminoalkyl nitrile converts the nitrile moiety to a carboxamide or a carboxylic acid group, depending upon the reaction conditions. For example, reaction of a biphenylyl aminoalkylnitrile such as N,N-di-n-butyl-3-cyano-3-(1,1'-biphenyl-2-yl)propylamine with an acid such as ninety percent (v/v) aqueous sulfuric acid for about two to about four hours at a temperature of about 80° to 120° C. converts the cyano group to a carboxamide, thus providing, for instance, N,N-di-n-butyl-3-aminocarbonyl-3-(1,1'-biphenyl-2-yl)propylamine. When the reaction is carried out for a longer period of time, for instance for about eight hours or longer, the product is the corresponding carboxylic acid, namely N,N-di-n-butyl-3-hydroxycarbonyl-3-(1,1'-biphenyl-2-yl)propylamine. The product in either case is isolated by the same procedure, namely by neutralizing the reaction mixture by the addition of a base such as sodium hydroxide, followed by extraction of the product into a water immiscible solvent such as diethyl ether. Evaporation of the organic solvent then affords the product, generally as a solid which can be crystalized from common solvents such as hexane or Skelly-B.

The carboxylic acids which are thus formed are readily esterified by conventional methods, for instance by reaction with a lower alkyl diazo compound such as diazomethane, or by reaction with an alcohol such as ethanol or hexanol in the presence of a mineral acid such as hydrochloric acid or sulfuric acid.

The β-hydroxybiphenylylalkylamines of this invention, compounds defined by the above general formula when Z is $$-(CH_2)_{n-2}\overset{\underset{\displaystyle |}{OH}}{C}H-CH_2-,$$

are prepared by reacting an amine of the formula $HNR^3R^4$ with a ω-biphenylyl-1,2-epoxy alkane. The epoxyalkane is derived by peracid oxidation of the corresponding ω-biphenylyl-1-alkene, which in turn is prepared by coupling an alkenyl halide with a biphenylyl methyl halide. The overall reaction is depicted by the following scheme:

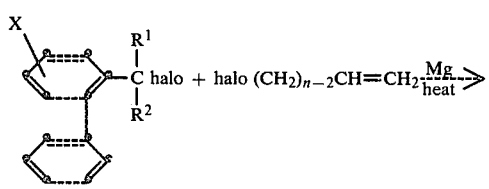

-continued

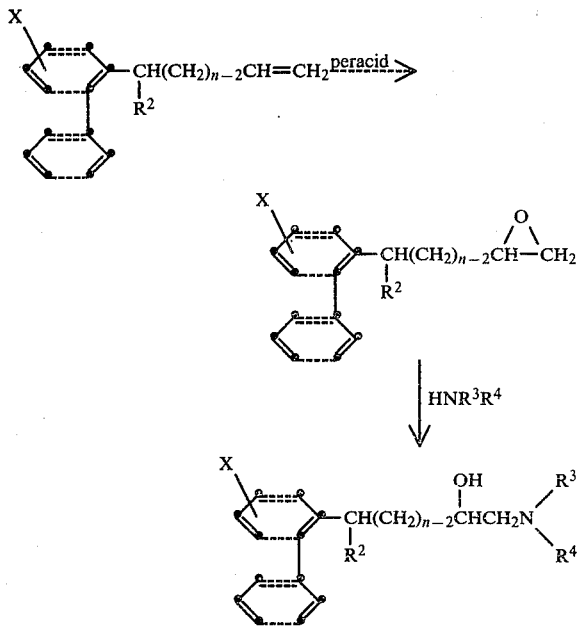

in which n, X, $R^1$, $R^2$, $R^3$ and $R^4$ are as defined above, and halo is a leaving group such as chloro, bromo or iodo. The above process is preferably utilized when $R^1$ is hydrogen. Compounds wherein $R^1$ is other than hydrogen are prepared by a related process which comprises reacting an alkenyl Grignard reagent with a biphenylylaldehyde or ketone to give the corresponding alcohol of the formula

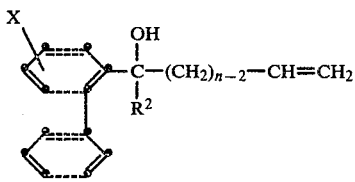

The alcohol compound thus formed can be converted to the corresponding nitrile, amide or carboxylic acid by conventional techniques, for example by halogenation with a phosphorous trihalide such as $PBr_3$, followed by reaction with NaCN to generate the corresponding nitrile and optional hydrolysis to produce the amide or carboxylic acid derivatives. Such compounds may be converted into the corresponding epoxides by treatment with meta-perchlorobenzoic acid. For conversion of the alkenyl alcohol compound to the epoxide it may be necessary to first protect the OH group, for example by forming the silyl ether of the formula

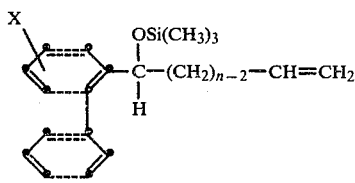

The silyl ether epoxide when formed may be reacted directly with the amine $HNR^3R^4$ to produce a compound of the invention wherein $R^1$ is OH, or can first be deprotected by hydrolysis.

The condensation of an amine with a ω-biphenylyl-1,2-epoxyalkane generally is accomplished by mixing the epoxide with about a two to three molar excess of the amine in a solvent such as ethanol. The reaction can be carried out in a bomb at a temperature of about 100° to about 200° C., and generally is substantially complete within about eight to sixteen hours. The product is isolated by evaporation of the reaction solvent, and further purification is accomplished by distillation, salt formation or the like.

Biphenylylalkylamines defined by the above general formula wherein $R^1$ is hydrogen and Z is —$(CH_2)_n$— are prepared from the corresponding biphenylyl alkanolamines wherein $R^1$ is hydroxy by dehydration to form the corresponding biphenylyl alkenylamines, followed by reduction of the olefinic double bond. For example, a biphenylyl alkanolamine such as N-methyl-N-(2-phenethyl)-3-hydroxy-3-(4-bromo-1,1'-biphenyl-2-yl)propylamine can be dehydrated by reaction with sulfuric acid to provide N-methyl-N-(2-phenethyl)-3-(4-bromo-1,1'-biphenyl-2-yl)-2-propenylamine. Hydrogenation of the latter compound over a suitable catalyst such as palladium on carbon affords the corresponding biphenylyl alkylamine, namely N-methyl-N-(2-phenethyl)-3-(4-bromo-1,1'-biphenyl-2-yl)propylamine.

The biphenylyl alkylamines comprehended by this invention which bear readily removable groups on the amine nitrogen atom (i.e. $R^3$ or $R^4$ is a readily removable group) are useful both as antiarrhythmic agents and as intermediates. Typical nitrogen substituents which are readily removable include methyl and benzyl. For example, an N-benzyl amine can be de-benzylated by hydrogenation over a catalyst such as palladium on carbon. N-methyl amines can be de-methylated by reaction with a haloformate followed by basic hydrolysis. Any of the above-described processes for preparing compounds of the invention can be carried out so as to provide N-methyl or N-benzyl biphenylyl alkylamines. Such compounds can be de-methylated or de-benzylated to provide compounds of the above general formula wherein one or both of $R^3$ and $R^4$ are hydrogen. Such compounds then can be re-alkylated as desired to provide any of a number of the other compounds of the invention. For example, a compound such as N-benzyl-N-isopropyl-4-cyano-4-(5-chloro-1,1'-biphenyl-2-yl)-butylamine can be de-benzylated by hydrogenation to provide the corresponding secondary amine, N-isopropyl-4-cyano-4-(5-chloro-1,1'-biphenyl-2-yl)butylamine. The secondary amine then can be re-alkylated, for instance by reaction with an alkyl halide such as n-pentyl bromide or n-propyl iodide, an alkenyl halide such as allyl bromide, 3-pentenyl iodide or 2-methyl-2-butenyl bromide, or with a phenylalkyl halide such as 2-phenethyl bromide or 3-phenylpropyl iodide. Such alkylation process is a convenient method for preparing a wide variety of biphenylyl alkylamines from a common starting material.

As already pointed out, the biphenylyl alkylamines provided by this invention are basic in nature and thus react with acids to form pharmaceutically acceptable acid addition salts. The salts are prepared by simply mixing the biphenylyl alkylamines with appropriate acids in suitable organic solvents such as diethyl ether. The acid addition salts normally crystallize out of solution and can be collected by filtration and recrystallized if desired.

When the biphenylyl alkylamines comprehended by this invention are tertiary amines, i.e. when $R^3$ and $R^4$ in the above general formula both are other than hydrogen, quaternary ammonium salts are readily formed by reaction with a lower alkyl alkylating agent. For example, reaction of a tertiary amine such as N,N-dimethyl-3-aminocarbonyl-3-(1,1'-biphenylyl-2-yl)propylamine with an alkylating agent such as allyl bromide in a suitable solvent such as dichloromethane effects quaternization to afford N-allyl-N,N-dimethyl-3-aminocarbonyl-3-(1,1'-biphenyl-2-yl)propylammonium bromide. Such quaternary salts are characteristically highly crystalline solids, and are included within the scope of this invention as antiarrhythmic agents.

The following list of 1,1'-biphenyl-2-yl propyl, butyl and pentylamines is illustrative of the compounds comprehended and provided by this invention.

N-isopropyl-4-hydroxy-4-(1,1'-biphenyl-2-yl)butylamine;

N-methyl-N-n-propyl-4-hydroxy-4-(3-fluoro-1,1'-biphenyl-2-yl)butylamine;

N-n-hexyl-4-cyano-4-(1,1'-biphenyl-2-yl)butylamine;

N,N-dimethyl-3-hydroxy-3-(1,1'-biphenyl-2-yl)propylamine;

N-allyl-3-cyano-3-(1,1'-biphenyl-2-yl)propylamine;

N-(3-hexenyl)-N-(2-phenethyl)-4-aminocarbonyl-4-(5-bromo-1,1'-biphenyl-2-yl)butylamine;

N,N-di-n-propyl-4-hydroxycarbonyl-4-(1,1'-biphenyl-2-yl)butylamine;

N,N-diisopropyl-5-(1,1'-biphenyl-2-yl)pentylaminium chloride;

N-tert-butyl-4-(5-bromo-1,1'-biphenyl-2-yl)-2-hydroxybutylamine;

N-isopentyl-N-methyl-5-hydroxy-5-methyl-5-(5-chloro-1,1'-biphenyl-2-yl)-2-hydroxypentylamine;

N-isohexyl-N-ethyl-3-isopropoxycarbonyl-3-methyl-3-(1,1'-biphenyl-2-yl)propylamine;

N,N-di-n-butyl-4-aminocarbonyl-4-ethyl-4-(3-fluoro-1,1'-biphenyl-2-yl)-2-hydroxybutylamine;

N,N,N-trimethyl-3-hydroxy-3-(1,1'-biphenyl-2-yl)propylammonium bromide;

d-N,N-diethyl-4-aminocarbonyl-4-(1,1'-biphenyl-2-yl)butylamine;

l-N,N-di-n-pentyl-4-hydroxycarbonyl-4-(5-bromo-1,1'-biphenyl-2-yl)butylamine;

dl-N,N-di-n-hexyl-4-cyano-4-(1,1'-biphenyl-2-yl)butylamine;

N-(3-pentenyl)-N-n-propyl-3-cyano-3-(1,1'-biphenyl-2-yl)propylamine;

N-ethyl-N-methyl-N-n-propyl-4-cyano-4-(5-chloro-1,1'-biphenyl-2-yl)butylammonium tosylate;

N-(3-phenylpropyl)-N-allyl-4-hydroxycarbonyl-4-(1,1'-biphenyl-2-yl)butylaminium acetate;

N,N-dimethyl-4-(1,1'-biphenyl-2-yl)-2-hydroxybutylaminium citrate;

1-[3-cyano-3-(5-fluoro-1,1'-biphenyl-2-yl)propyl]piperidine;

N,N-diethyl-4-hydroxycarbonyl-4-(5-fluoro-1,1'-biphenyl-2-yl)butylamine;

N-benzyl-N-isopropyl-3-aminocarbonyl-3-(1,1'-biphenyl-2-yl)propylamine;

1-(3-methylpentyl)-1-ethyl-4-aminocarbonyl-4-(1,1'-biphenyl-2-yl)pyrrolidinium phosphate;

N-allyl-N-(3-phenylpropyl)-N-n-propyl-4-methyl-4-(1,1'-biphenyl-2-yl)-2-hydroxybutylammonium iodide;

N-benzyl-N-(2-phenethyl)-3-cyano-3-(1,1'-biphenyl-2-yl)propylamine;

N,N-dimethyl-5-cyano-5-(6-chloro-1,1-biphenyl-2-yl)-2-hydroxypentylamine;

N-isopropyl-5-aminocarbonyl-5-ethyl-5-(1,1'-biphenyl-2-yl)pentylamine;

N-benzyl-5-methoxycarbonyl-5-isopropyl-5-(1,1'-biphenyl-2-yl)pentylaminium bromide; and N-isopropyl-4-ethoxycarbonyl-4-(1,1'-biphenyl-2-yl)butylamine.

The biphenylyl alkylamines of this invention are useful as antiarrhythmic agents. That the compounds of the invention are potent antiarrhythmic agents has been demonstrated in dogs suffering from ouabain induced cardiac arrhythmias. In a typical experiment, one or more mongrel dogs of either sex were anesthetized with sodium pentobarbital. A 23 guage Butterfly infusion needle was placed in the radial vein for the introduction into the dog of sufficient ouabain to induce an arrhythmia, and for the introduction into the dog of the test compound. Each dog was continuously monitored throughout the experiment by electrocardiogram. After the ouabain induced cardiac arrhythmia had continued for thirty minutes, a compound of this invention was administered via the Butterfly infusion needle at the rate of 200 μg per kilogram of dog body weight per minute. If the arrhythmia was not converted to a normal sinus rhythm within ten minutes from the initial administration of test compound, as observed by electrocardiogram, the rate of infusion of test compound was increased to 500 μg per kilogram per minute. When an arrhythmia conversion was noted, the infusion of test compound in general was continued until twice the amount of such compound which effected the conversion was administered to the dog. Following the complete administration of test compound to the dog, the dog's heart was monitored by electrocardiogram until such time that an arrhythmia returned to the dog's heart, or for a maximum time of two hours, at which time the experiment was terminated.

The results of several experiments are set out in the following table. Each compound listed in the table, and its corresponding biological evaluation, is designated by alphabetical letter given in the column marked "compound". Most of the compounds were evaluated more than once, as indicated in the "No. of Dogs" column. The amount of ouabain needed to induce an arrhythmia is given in μg per kilogram of dog body weight. The converting dose and total dose of test compound are given in mg. per kilogram of animal body weight. Duration of conversion is recorded in minutes.

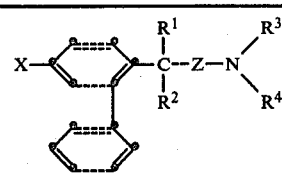

| Compound | X | $R^1$ | $R^2$ | Z | $R^3$ | $R^4$ | No. of Dogs |
|---|---|---|---|---|---|---|---|
| A | F | H | H | CH$_2$CH$_2$CH$_2$ | CH$_3$ | CH$_3$ | 2 |
| B | F | OH | H | CH$_2$CH$_2$CH$_2$ | Et | Et | 3 |
| C | F | OH | H | CH$_2$CH$_2$CH$_2$ | H | iPr | 4 |
| D | Cl | OH | H | CH$_2$CH$_2$CH$_2$ | CH$_3$ | CH$_3$ | 3 |
| E | H | OH | H | CH$_2$CH$_2$ | CH$_3$ | CH$_3$ | 2 |
| F | H | OH | H | CH$_2$CH$_2$CH$_2$ | 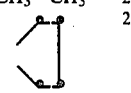 | | 2 |

-continued

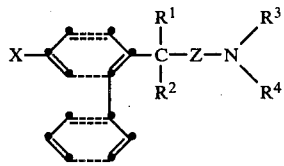

| | R¹ | | R² | Z | R³ | R⁴ | |
|---|---|---|---|---|---|---|---|
| G | H | COOH | H | CH₂CH₂CH₂ | CH₃ | CH₃ | 2 |
| H | H | CN | H | CH₂CH₂CH₂ | CH₃ | CH₃ | 1 |
| I | H | H | H | OH<br>\|<br>CH₂CHCH₂ | | iPr | iPr | 4 |
| J | H | CONH₂ | H | CH₂CH₂CH₂ | CH₃ | CH₃ | 2 |

| Compound | Ouabain μg/Kg | Converting dose mg/Kg | Total Dose mg/Kg | Duration of Conversion minutes |
|---|---|---|---|---|
| A | 80 | 4.0 | 8.0 | 12 |
|   | 85 | 3.4 | — | — |
| B | 85 | 2.5 | 5.0 | 32 |
|   | 75 | 5.8 | 11.5 | 120+ |
|   | 75 | 3.5 | 7.0 | 18 |
| C | 60 | 2.8 | 5.5 | 120+ |
|   | 70 | 8.0 | 9.5 | 85+ |
|   | 80 | 3.0 | 6.0 | 65 |
|   | 70 | 3.0 | 6.0 | 105+ |
| D | 70 | 2.5 | 5.0 | 5 |
|   | 60 | 0.9 | 1.8 | 120+ |
|   | 70 | 6.0 | 10.0 | 43+ |
| E | 70 | 8.5 | 8.7 | 3 |
|   | 60 | 1.8 | 3.6 | 51 |
| F | 60 | 2.5 | 5.0 | 93 |
|   | 70 | 3.0 | 6.0 | 42 |
| G | 60 | 4.8 | 9.5 | 45 |
|   | 75 | 10.0 | 10.0 | — |
| H | 70 | 6.3 | 10.5 | 13 |
| I | 60 | 1.9 | 3.8 | 83 |
|   | 55 | 2.0 | 4.0 | 48 |
|   | 70 | 1.5 | 3.0 | 26 |
|   | 65 | 1.6 | 3.2 | 23 |
| J | 70 | 2.6 | 5.2 | 53 |
|   | 60 | 1.9 | 3.8 | 120+ |

Pharmaceutical formulations containing the biphenylyl alkylamines of this invention are provided as a further embodiment of the invention. Such formulations comprise an antiarrhythmic amount of a compound having the above general formula in combination with a pharmaceutical carrier therefor. The active ingredient will be admixed with a carrier in a ratio of from about 1 to about 50 percent by weight. The compounds of the invention can be administered parenterally, for example in the form of liquid injectable solutions or suspensions, or orally in the form of solid compositions which are molded into tablets or encapsulated in gelatin capsules. Pharmaceutical carriers, diluents and excipients commonly used for formulating solid compositions include starch, glucose, lactose, gelatin, malt, rice flour, silica gel, hydroxyethyl cellulose, magnesium carbonate, sodium benzoate, and related carriers. Carriers employed in liquid formulations include ethanol, saline, sterile water, glucose syrup, syrup of acacia, peanut oil, wheat germ oil, sorbitan trioleate, ethyl oleate, lecithin and the like. The injectable compositions can be formulated for convenient parenteral administration via the intramuscular, subcutaneous or, preferably, the intravenous routes.

An additional aspect of this invention is a method for treating subjects suffering from an arrhythmia and in need of treatment and a method of providing prophylaxis to subjects suspected of developing an arrhythmia. The method of treatment is carried out by administering an effective dose of a biphenylyl alkylamine of this invention to a subject to be treated. The effective amount of antiarrhythmic agent to be administered may vary depending upon the route of administration, whether or not a subject is suffering from an arrhythmia at the time of administration, the severity of the arrhythmia, the patient being treated and related factors. A subject suffering from an arrhythmia and in need of treatment normally is administered a dose of antiarrhythmic agent sufficient to effect a conversion to normal sinus rhythm. The compound of this invention typically is formulated for parenteral administration and is infused intravenously at a dose effective for causing a conversion of the arrhythmia. The compound then is administered as a maintenance dose, either parenterally or orally. The dose of active compound routinely used to effect a conversion of an arrhythmia is from about 0.1 to about 50 mg. per kg of animal body weight. A typical converting dose administered intravenously is from about 0.5 to about 20 mg. per kg. Maintenance therapy is accomplished by administering an active compound of this invention at the rate of from about 0.1 to about 35 mg. per kg. of animal body weight. A tablet well suited for oral maintenance therapy or prophylactic treatment of a human subject may contain, for example, from about 7 to about 750 mg. of a biphenylyl alkylamine of this invention in combination with a suitable carrier. Such tablet can be administered to such human at the rate of about one to three times each day for the effective control of cardiac arrhythmia.

The following operating examples are illustrative of specific aspects of the invention. The examples should not be construed as limiting the invention in any way.

EXAMPLE 1

N,N-Dimethyl-4-hydroxy-4-(5-fluoro-1,1'-biphenyl-2-yl)butylamine

A solution of 11.6 g. of 2-formyl-5-fluoro-1,1'-biphenyl in 500 ml. of dry tetrahydrofuran containing a Grignard reagent prepared by reacting 9.6 g. of magnesium with 25.3 g. of N,N-dimethyl-3-chloropropylamine was heated to reflux and stirred for five hours. The reaction mixture was cooled to room temperature, diluted with 200 ml. of saturated aqueous ammonium chloride, and then extracted several times with diethyl ether. The ethereal extracts were combined, washed with water and the solvent was removed by evaporation under reduced pressure to provide an oil. The oil was crystallized from Skelly-B to provide 9.5 g. of N,N-dimethyl-4-hydroxy-4-(5-fluoro-1,1'-biphenyl-2-yl)butylamine. M.P. 60°–62° C.

Analysis calc. for $C_{18}H_{22}FNO$: Theory: C, 75.23; H, 7.72; N, 4.87. Found: C, 75.07; H, 7.68; N, 4.93.

EXAMPLE 2

By a similar procedure, 2-formyl-1,1'-biphenyl was reacted with 3-dimethylaminopropyl magnesium chloride hydrochloride to provide N,N-dimethyl-4-hydroxy-4-(1,1'-biphenyl-2-yl)butylaminium chloride. M.P. 161°–164° C.

Analysis calc. for $C_{18}H_{24}ClNO$: Theory: C, 70.69; H, 7.91; N, 4.58. Found: C, 70.47; H, 7.85; N, 4.59.

EXAMPLE 3

N-Isopropyl-4-hydroxy-4-[(1,1'-biphenyl)-2-yl]-2-butynylamine

A solution of 7.8 g. of N-isopropyl-2-propynylamine in 500 ml. of dry tetrahydrofuran was stirred and cooled to −80° C. in a dry ice and acetone bath. To the cold stirred reaction mixture was added dropwise over thirty minutes 62.5 ml. of a 1.6 molar solution of n-butyl lithium in tetrahydrofuran. Following complete addition, the reaction mixture was stirred at −80° C. for one hour. A solution of 7.3 g. of 2-formylbiphenyl in 500 ml. of tetrahydrofuran next was added dropwise over one hour to the cold stirred reaction mixture. Following complete addition of the aldehyde solution, the reaction mixture was stirred for an additional hour at −80° C. and then heated to reflux and stirred for sixteen hours. After cooling the reaction mixture to room temperature, 500 ml. of water was added slowly to decompose any remaining n-butyl lithium. The product next was extracted into diethyl ether, and the ethereal extracts were combined and washed with water. The product then was extracted into 6 N hydrochloric acid solution. The acidic extracts were combined and made alkaline by the addition of 10 percent aqueous sodium hydroxide. The alkaline layer was extracted several times with fresh diethyl ether, and the ethereal extracts were combined, washed with water and dried. Removal of the solvent by evaporation under reduced pressure provided 4.2 g. of N-isopropyl-4-hydroxy-4-[(1,1'-biphenyl)-2-yl]-2-butynylamine. M.P. 116°–119° C.

Analysis calc. for $C_{19}H_{21}NO$: Theory: C, 81.68; H, 7.58; N, 5.01. Found: C, 81.78; H, 7.45; N, 4.93.

EXAMPLES 4–11

The following 4-hydroxy-4-[(1,1'-biphenyl)2-yl]-2-butynylamines were prepared from the appropriate propynylamine and formylbiphenyl according to the general procedure set out in Example 3.

N,N-Diethyl-4-hydroxy-4-[(5-fluoro-1,1'-biphenyl)-2-yl]-2butynylamine. M.P. 133°–136° C.

N,N-Diisopropyl-4-hydroxy-4-[(5-fluoro-1,1'-biphenyl)-2-yl]-2-butynylamine. M.P. 149°–151° C.

N-isopropyl-N-methyl-4-hydroxy-4-[(1,1'-biphenyl)-2-yl]-2-butynylamine. M+ 293.

N,N-Diisopropyl-4-hydroxy-4-[(1,1'-biphenyl)-2-yl]-2-butynylamine.

N-tert-Butyl-4-hydroxy-4-[(1,1'-biphenyl)-2-yl]-2-butynylamine.

N,N-Diethyl-4-hydroxy-4-[(1,1'-biphenyl)-2-yl]-2-butynylamine.

1-(4-hydroxy-4-[(1,1'-biphenyl)-2-yl]-2-butynyl)pyrrolidine.

N-Isopropyl-4-hydroxy-4-[(5-fluoro-1,1'-biphenyl)-2-yl]-2-butynylamine.

EXAMPLE 12

N-Isopropyl-4-hydroxy-4-[(5-fluoro-1,1'-biphenyl)-2-yl]butylamine

A solution of 9.0 g. of N-isopropyl-4-hydroxy-4-[(5-fluoro-1,1'-biphenyl)-2-yl]-2-butynylamine in 200 ml. of ethanol containing 3.0 g. of five percent palladium suspended on carbon was shaken for two hours at 24° C. in a Parr hydrogenator under an initial hydrogen pressure of 40 psi. The reaction mixture then was filtered and the filtrate was concentrated to an oil by evaporation of the solvent under reduced pressure. The oil was dissolved in 200 ml. of ethyl acetate, and the product was then extracted into 6N hydrochloric acid. The acidic layer was separated, washed with fresh ethyl acetate, and then basified by the addition of 5N sodium hydroxide. The alkaline reaction mixture was extracted several times with diethyl ether, and the ethereal extracts were combined, washed with water and dried. Removal of the solvent by evaporation under reduced pressure afforded a solid which was recrystallized from ethanol to give 1.0 g. of N-Isopropyl-4-hydroxy-4-[(5-fluoro-1,1'-biphenyl)-2-yl]butylamine. M.P. 88°–91° C.

Analysis calc. for $C_{19}H_{24}FNO$: Theory: C, 75.71; H, 8.03; N, 4.65. Found: C, 75.65; H, 8.25; N, 4.64.

EXAMPLES 13–17

According to the general procedure set out in Example 12, the following alkylamines were prepared by hydrogenating the appropriate unsaturated amine:

N,N-Diethyl-4-hydroxy-4-[(5-fluoro-1,1'-biphenyl)-2-yl]butylamine. B.P. 168°–174° 1 C. at 0.4 torr.

Analysis calc. for $C_{20}H_{26}FNO$: Theory: C, 76.16; H, 8.31; N, 4.44. Found: C, 75.97; H, 8.52; N, 4.67.

N,N-Diethyl-4-hydroxy-4-[(1,1'-biphenyl)-2-yl]butylamine. B.P. 162°–165° C. at 0.4 torr.

Analysis calc. for $C_{20}H_{27}NO$: Theory: C, 80.76; H, 9.15; N, 4.71. Found: C, 80.98; H, 8.90; N, 4.84.

N-Isopropyl-N-methyl-4-hydroxy-4-[(1,1'-biphenyl)-2-yl]butylamine. M.P. 50°–53° C.

Analysis calc. for $C_{20}H_{27}NO$: Theory: C, 80.76; H, 9.15; N, 4.71. Found: C, 80.55; H, 9.10; N, 4.48.

N-Isopropyl-4-hydroxy-4-[(1,1'-biphenyl)-2-yl]butylamine. M.P. 120°–121.5° C.

Analysis calc. for $C_{19}H_{25}NO$: Theory: C, 80.52; H, 8.89; N, 4.94. Found: C, 80.51; H, 8.64; N, 5.17.

1-(4-hydroxy-4-[(1,1'-biphenyl)-2-yl]pyrrolidine. M.P. 78°–80° C.

Analysis calc. for $C_{20}H_{25}NO$: Theory: C, 81.31; H, 8.53 N, 4.74. Found: C, 81.12; H, 8.26; N, 4.86.

EXAMPLE 18

N-tert-Butyl-4-hydroxy-4-[(5-fluoro-1,1'-biphenyl)-2-yl]butylaminium chloride To a stirred solution of 5.0 g. of N-tert-butyl-4-hydroxy-4-[(5-fluoro-1,1'-biphenyl)-2-yl]butylamine in 200 ml. of diethyl ether was added excess hydrogen chloride. The precipitate which formed was collected by filtration and recrystallized from ethanol and diethyl ether to provide 3.2 g. of N-tert-butyl-4-hydroxy-4-[(5-fluoro-1,1'-biphenyl)-2-yl]butylaminium chloride. M.P. 143°–145° C.

Analysis calc. for $C_{20}H_{27}ClFNO$: Theory: C, 68.26; H, 7.73; N, 3.98. Found: C, 68.03; H, 7.98; N, 3.92.

EXAMPLES 19–23

The following amine acid addition salts were prepared according to the method described in Example 18.

N,N-Diisopropyl-4-hydroxy-4-[(5-fluoro-1,1'-biphenyl)-2-yl]butylaminium chloride. M.P. 153°–155° C.

Analysis calc. for $C_{22}H_{32}ClFNO$: Theory: C, 69.55; H, 8.22; N, 3.69. Found: C, 69.34; H, 8.19; N, 3.61.

N-Isopropyl-4-hydroxy-4-methyl-4-(1,1'-biphenyl-2-yl)butylaminium chloride. M.P. 185°–186° C.

Analysis calc. for $C_{20}H_{28}ClNO$: Theory: C, 71.94; H, 8.45; N, 4.19. Found: C, 71.84; H, 8.48; N, 4.02.

N-Isopropyl-4-methyl-4-(1,1'-biphenyl-2-yl)butylaminium chloride. M.P. 182°–183° C.

Analysis calc. for $C_{20}H_{28}ClNO$: Theory: C, 75.56; H, 8.88; N, 4.41. Found: C, 75.83; H, 8.57; N, 4.20.

N,N-Diisopropyl-4-hydroxy-4-(1,1'-biphenyl-2-yl)butylaminium chloride. M.P. 172°–174° C.

Analysis calc. for $C_{22}H_{32}ClNO$: Theory: C, 73.00; H, 8.91; N, 3.87. Found: C, 72.80; H, 8.61; N, 3.93.

N-Isopropyl-N-methyl-4-hydroxy-4-(1,1'-biphenyl-2-yl)butylaminium chloride. M.P. 130°–133° C.

Analysis calc. for $C_{20}H_{28}ClNO$: Theory: C, 71.94; H, 8.45; N, 4.19. Found: C, 72.08; H, 8.22; N, 3.92.

EXAMPLE 24

N,N-Dimethyl-3-hydroxy-3-(1,1'-biphenyl-2-yl)propylamine

A solution of 10.1 g. of 2-acetyl-1,1'-biphenyl in 100 ml. of ethanol containing 7.6 g. of paraformaldehyde, 9.7 g. of dimethylaminium chloride and one drop of concentrated hydrochloric acid was heated to reflux and stirred for sixteen hours. After cooling the reaction mixture to room temperature, the solvent was removed by evaporation. The residue thus formed was crystallized from ethanol and diethyl ether to give 3.6 g of N,N-dimethyl-3-oxo-3-(1,1'-biphenyl-2-yl)propylaminium chloride. M.P. 130°–131° C.

To a cold (0° C.) stirred solution of N,N-dimethyl-3-oxo-3-(1,1'-biphenyl-2-yl)propylamine in 300 ml. of methanol was added protion-wise over thirty minutes 1.9 g. of sodium borohydride. Following complete addition of the reducing agent, the reaction mixture was warmed to room temperature and stirred for sixteen hours, and then heated to reflux and stirred for an additional three hours. The reaction mixture was cooled to 25° C. and concentrated to dryness by evaporation of the solvent under reduced pressure, thus providing a solid. The solid so formed was recrystallized from Skelly B solvent to afford 1.5 g. of N,N-dimethyl-3-hydroxy-3-(1,1'-biphenyl-2-yl)propylamine. M.P. 80°–82° C.

Analysis calc. for $C_{17}H_{21}NO$: Theory: C, 79.96; H, 8.29; N, 5.49. Found: C, 80.25; H, 8.49; N, 5.22.

EXAMPLE 25

N,N-Dimethyl-4-cyano-4-(1,1'-biphenyl-2-yl)butylamine

To a stirred solution of 3.5 g. of sodium amide in 250 ml. of dry toluene was added dropwise over thirty minutes a solution of 16.7 g. of (1,1'-biphenyl-2-yl)acetonitrile in 200 ml. of toluene. The reaction mixture was heated to reflux and stirred for three hours following complete addition of the nitrile. The reaction mixture next was cooled to room temperature, and to the stirred solution was added dropwise over one hour a solution of 17.4 g. of N,N-dimethyl-3-chloropropylamine in 200 ml. of dry toluene. When the addition was complete, the reaction mixture was heated to reflux and stirred for sixteen hours. After cooling the reaction mixture to room temperature, it was added to 500 ml. of ice water. The product was extracted from the aqueous mixture into diethyl ether, and the ethereal extracts were combined, washed with water and then extracted several times with 6 N hydrochloric acid. The acidic extracts were combined, washed with fresh diethyl ether and then made alkaline with 10% sodium hydroxide. The alkaline solution was extracted with fresh diethyl ether, and the ethereal extracts were combined, washed with water and dried. Removal of the solvent by evaporation under reduced pressure and distillation of the product provided 11.3 g. of N,N-dimethyl-4-cyano-4-(1,1'-biphenyl-2-yl)butylamine. B.P. 157°–162° C. at 0.5 torr.

Analysis calc. for $C_{19}H_{22}N_2$: Theory: C, 81.97; H, 7.97; N, 10.06. Found: C, 81.74; H, 7.71; N, 9.89.

EXAMPLES 26–27

Following the procedure set forth in Example 25, the following cyano-aralkyl amines were prepared.

N,N-Diisopropyl-4-cyano-4-(1,1'-biphenyl-2-yl)butylamine. B.P. 75°–185° C. at 0.3 torr. M+334.

N-Benzyl-N-isopropyl-4-cyano-4-(1,1'-biphenyl-2-yl)butylamine. B.P. 195°–204° C. at 0.1 torr. M+ 382.

EXAMPLE 28

N,N-Dimethyl-4-aminocarbonyl-4-(1,1'-biphenyl-2-yl)butylamine

A solution of 2.4 g. of N,N-dimethyl-4-cyano-4-(1,1'-biphenyl-2-yl)butylamine in 20 ml. of concentrated sulfuric acid containing 5 ml. of water was heated on a steam bath for four hours. The reaction mixture then was cooled to 5° C. and made alkaline by the addition of 10% sodium hydroxide. The aqueous alkaline solution was extracted several times with diethyl ether. The ethereal extracts were combined, washed with water and dried. Removal of the solvent by evaporation under reduced pressure afforded a solid, which upon recrystallization from benzene and Skelly-B solvent provided 600 mg. of N,N-dimethyl-4-aminocarbonyl-4-(1,1'-biphenyl-2-yl)butylamine. M.P. 108°–110° C.

Analysis calc. for $C_{19}H_{24}N_2O$: Theory: C, 76.99; H, 8.16; N, 9.45. Found: C, 76.70; H, 7.94; N, 9.24.

EXAMPLES 29–30

Following the procedure of Example 28, the following amides were prepared by acid hydrolysis of the corresponding nitriles:

N,N-Diisopropyl-4-aminocarbonyl-4-(1,1'-biphenyl-2-yl)butylamine. M.P. 70°–72° C.

Analysis calc. for $C_{23}H_{32}N_2O$: Theory: C, 78.36; H, 9.15; N, 7.95. Found: C, 78.08; H, 8.89; N, 7.71.

N-Benzyl-N-isopropyl-3-aminocarbonyl-3-(1,1'-biphenyl-2-yl)butylamine.

EXAMPLE 31

N,N-Dimethyl-4-hydroxycarbonyl-4-(1,1'-biphenyl-2-yl)butylamine

A solution of 6.0 g. of N,N-dimethyl-4-cyano-4-(1,1'-biphenyl-2-yl)butylamine in 65 ml. of 90% sulfuric acid was heated on a steam bath for eight hours. After cooling the reaction mixture to 5° C. and making it alkaline by the addition of 10% sodium hydroxide, the product was extracted therefrom into diethyl ether. The ethereal extracts were washed with water and dried. Excess hydrogen chloride was bubbled into the ethereal solution, whereupon a precipitate formed and was collected by filtration. Crystallization of the precipitate from ethanol afforded 2.9 g. of N,N-dimethyl-4-hydroxycarbonyl-4-(1,1'-biphenyl-2-yl)butylaminium chloride. M.P. 192°–194° C.

Analysis calc. for $C_{19}H_{24}ClNO_2$: Theory: C, 68.35; H, 7.25; N, 4.20; O, 9.58. Found: C, 68.18; H, 7.19; N, 4.39; O, 10.00.

EXAMPLE 32

N,N-Diisopropyl-2-hydroxy-4-(1,1'-biphenyl-2-yl)butylamine

A solution of 4.0 g. of 1,2-epoxy-4-(1,1'-biphenyl-2-yl)butane in 50 ml. of ethanol containing 6.0 g. of diisopropylamine was heated to 160° C. in a reaction bomb and stirred at that temperature for sixteen hours. The reaction mixture was then cooled to room temperature and concentrated to an oil by evaporation of the solvent under reduced temperature. The oil was dissolved in 200 ml. of diethyl ether, washed with water and then extracted into 6 N hydrochloric acid. The acid layer was separated, washed with fresh diethyl ether, and then made alkaline by the addition of 10% sodium hydroxide. The alkaline solution was extracted several times with diethyl ether. The ethereal extracts were combined, washed with water and dried. Removal of the solvent by evaporation provided an oil, which upon distillation afforded 1.8 g. of N,N-Diisopropyl-2-hydroxy-4-(1,1'-biphenyl-2-yl)butylamine. B.P. 168°–171° C. at 0.2 torr.

Analysis calc. for $C_{22}H_{31}NO$: Theory: C, 81.18; H, 9.60; N, 4.30. Found: C, 81.42; H, 9.82; N, 4.26.

EXAMPLE 33

Following a precedure similar to that of Example 32, 1,2-epoxy-4-(1,1'-biphenyl-2-yl)butane was reacted with isopropylamine to provide N-isopropyl-2-hydroxy-4-(1,1'-biphenyl-2-yl)butylamine. The amine base so formed was reacted with hydrogen chloride to provide N-isopropyl-2-hydroxy-4-(1,1'-biphenyl-2-yl)butylaminium chloride. M.P. 153°–154° C.

Analysis calc. for $C_{19}H_{25}ClNO$: Theory: C, 71.34; H, 8.19; N, 4.38. Found: C, 71.21; H, 7.95; N, 4.36.

EXAMPLE 34

N,N-Dimethyl-4-(1,1'-biphenyl-2-yl)butylamine

A solution of 4.6 g. of N,N-dimethyl-4-hydroxy-4-(1,1'-biphenyl-2-yl)butylaminium chloride in 100 ml. of 4N sulfuric acid was heated to 100° C. and stirred for one hour. The reaction mixture was cooled to 5° C. and made alkaline by the addition of 10% sodium hydroxide. The alkaline solution was extracted with diethyl ether, and the ethereal extracts were combined, washed with water and dried. Evaporation of the solvent under reduced pressure afforded 3.3 g. of N,N-dimethyl-4-(1,1'-biphenyl-2-yl)-3-butenylamine.

A solution of 3.0 g. of N,N-dimethyl-4-(1,1'-biphenyl-2-yl)-3-butenylamine in 200 ml. of ethyl acetate containing 2.0 g. of five percent palladium on carbon was stirred for one hour at 25° C. under hydrogen at 40 psi. The reaction mixture then was filtered and the solvent was removed from the filtrate by evaporation to provide an oil. The oil was dissolved in 100 ml. of diethyl ether and stirred while excess hydrogen chloride was added to the solution. The precipitate which formed was collection by filtration and was recrystallized from ethanol and diethyl ether to provide 2.1 g. of N,N-dimethyl-4-(1,1'-biphenyl-2-yl)butylaminum chloride. M.P. 114°–116° C.

Analysis calc. for $C_{18}H_{24}ClNO$: Theory: C, 74.59; H, 8.35; N, 4.83. Found: C, 74.48; H, 8.30; N, 4.71.

EXAMPLE 35

N-Isopropyl-3-aminocarbonyl-3-(1,1'-biphenyl-2-yl)propylamine

A solution of 2.1 g. of N-benzyl-N-isopropyl-3-aminocarbonyl-3-(1,1'-biphenyl-2-yl)propylamine (from Example 30) in 200 ml. of ethanol containing 2.0 g. of five percent palladium suspended on carbon was stirred under a hydrogen pressure of 60 psi and heated to 40° C. for forty-five minutes. The reaction mixture then was filtered and the filtrate was concentrated in volume by evaporation of the solvent. The residue thus obtained was dissolved in diethyl ether, washed with water and then crystallized from Skelly-B to afford 150 mg. of N-isopropyl-3-aminocarbonyl-3-(1,1'-biphenyl-2-yl)-propylamine. M.P. 92°–95° C.

Analysis calc. for $C_{19}H_{24}N_2O$: Theory: C, 76.99; H, 8.16; N, 9.45. Found: C, 76.78; H, 8.14; N, 9.57.

EXAMPLE 36

Following a similar procedure, the appropriate N-benzyl amine was hydrogenated to give the following compound:

N-Isopropyl-4-aminocarbonyl-4-(1,1'-biphenyl-2-yl)butylamine. M.P. 121°–122° C.

Analysis calc. for $C_{20}H_{26}N_2O$: Theory: C, 77.38; H, 8.44; N, 9.02. Found: C, 77.19; H, 8.16; N, 8.91.

EXAMPLE 37

1-methyl-1-[4-hydroxy-4-(1,1'-biphenyl-2-yl)butyl]pyrrolidinium iodide

To a stirred solution of 3.0 g. of 1-[4-hydroxy-4-(1,1'-biphenyl-2-yl)butyl]pyrrolidine in 10 ml. of ethanol was added 1.3 g. of methyl iodide in one portion. The reaction mixture was stirred at room temperature for sixteen hours, and the solvent was then removed by evaporation under reduced pressure to provide an oil. The oil was crystallized from petroleum ether to provide 4.2 g. of 1-methyl-1-[4-hydroxy-4-(1,1'-biphenyl-2-yl)butyl]-pyrrolidinium iodide. M.P. 157°–159° C.

Analysis calc. for $C_{21}H_{28}INO$: Theory: C, 57.67; H, 6.45; N, 3.20. Found: C, 57.75; H, 6.19; N, 3.22.

EXAMPLE 38

The following quaternary ammonium salt was prepared by reacting the appropriate tertiary amine with an alkylating agent according to the method described in Example 37.

N,N-Dimethyl-N-isopropyl-4-hydroxy-4-(1,1'-biphenyl-2-yl)butylammonium iodide. M.P. 93°–95° C.

Analysis calc. for $C_{21}H_{30}INO$: Theory: C, 57.41; H, 6.88; N, 3.19. Found: C, 56.93; H, 6.69; N, 3.19.

EXAMPLE 39

N,N-Dimethyl-4-hydroxy-4-[(5-chloro-1,1'-biphenyl)-2-yl]butylaminium chloride

Magnesium (5.0 g., 0.21 mole) was added to a 3-liter, 3-necked flask equipped with a stirrer and thermometer. Sufficient ether was added just to cover the magnesium and this was followed by the slow addition of a little ethylene dibromide to activate the mixture. N,N-dimethyl-3-chloropropylamine (31.6 g., 0.2 mole) dissolved in diethyl ether was then added to the reaction mixture which was stirred at room temperature until substantially all of the magnesium had dissolved. 2-Phenyl-4-chlorobenzaldehyde (48.7 g., 0.23 mole) dissolved in diethylether was then added dropwise and the reaction mixture stirred overnight. Next morning, the reaction mixture was refluxed gently for about three hours. This was followed by decomposition with saturated ammonium chloride and addition to diethyl ether, extraction with 6 N HCl, basification with 10% NaOH and repeat extraction with diethyl ether, washing with water and drying with sodium sulphate. After concentration a solid crystallized out and this was dissolved in diethyl ether and converted to the title product with HCl, m.p. 119°–121° C., yield 13.7 g.

EXAMPLE 40

N,N-Dimethyl-4-[(5-chloro-1,1'-biphenyl)-2-yl]-3-butenylaminium chloride

The product of Example 39 (3.0 g., 0.1 mole) was refluxed for six hours in 4 N $H_2SO_4$ (80 ml.) in a 250 ml. flask with stirring. The reaction mixture was then cooled and added to ice water, basified with 10% NaOH, extracted with diethyl ether, washed with water, dried with $Na_2SO_4$ and concentrated down. The base thereby formed was converted into a hydrochloride (the title compound) and then recrystallized from ethanol and diethyl ether, m.p. 149.5° to 150° C., yield 1.6 g.

EXAMPLE 41

N,N-Dimethyl-4-[(5-chloro-1,1'-biphenyl)-2-yl]butylaminium chloride

N,N-Dimethyl-4-[(5-chloro-1,1'-biphenyl)-2-yl]-3-butenylaminium chloride (8.4 g., 0.011 mole) was hydrogenated in the presence of 5% palladium on charcoal (1.0 g.) in ethanol (200 ml.) using a procedure similar to that of Example 34, m.p. 131°–133° C., yield 1.8 g.

EXAMPLE 42

Preparation of 5-cyano-5-(1,1'-biphenyl-2-yl)pentyl chloride

To a stirred solution of 4.3 g. of sodium amide in 300 ml. of toluene was added dropwise over thirty minutes a solution of 19.3 g. of (1,1'-biphenyl-2-yl)acetonitrile in 200 ml. of toluene. The reaction mixture was heated at reflux for three hours, and then cooled to room temperature and stirred while a solution of 18.1 g. of 4-bromobutyl chloride in 50 ml. of toluene was added dropwise over thirty minutes. Following complete addition, the reaction mixture was heated again to reflux and stirred for sixteen hours. The reaction mixture next was cooled to room temperature and added to 500 ml. of ice water. The product was extracted from the aqueous mixture into diethyl ether. The ethereal extracts were combined and the solvent was removed by evaporation to provide the product as an oil. The oil was distilled to give 16.5 g. of 5-cyano-5-(1,1'-biphenyl-2-yl)pentyl chloride. B.P. 141°–165° C. at 0.06 torr.

EXAMPLE 43

N-Isopropyl-5-cyano-5-(1,1'-biphenyl-2-yl)pentylamine

A mixture of 13.7 g. of 5-cyano-5-(1,1'-biphenyl-2-yl)pentyl chloride from Example 42, 2 g. of potassium iodide and 100 ml. of isopropylamine was heated at 150° C. for twelve hours in a reaction bomb. After cooling the reaction mixture to room temperature, it was diluted with 200 ml. of diethyl ether. The ethereal solution was washed with water, and then extracted with two 100 ml. portions of 6 N hydrochloric acid. The acidic extracts were combined, made alkaline with dilute sodium hydroxide, and the product was extracted therefrom into diethyl ether. The ethereal solution was washed with water, dried, and then saturated with hydrogen chloride to give as a white crystalline solid 4.9 g. of N-isopropyl-5-cyano-5-(1,1'-biphenyl-2-yl)pentylaminium chloride. M.P. 143°–145° C.

Analysis calc. for $C_{21}H_{27}ClN_2$: Theory: C, 73.56; H, 7.94; N, 8.17. Found: C, 73.49; H, 8.17; N, 8.16.

EXAMPLE 44

N-Isopropyl-5-aminocarbonyl-5-(1,1'-biphenyl-2-yl)pentylamine

A solution of 4.9 g. of N-isopropyl-5-cyano-5-(1,1'-biphenyl-2-yl)pentylaminium chloride in 18.0 g. of conc. sulfuric acid containing 2.0 g. of water was heated at 100° C. for three hours. After cooling the reaction mixture to 5° C., the mixture was made alkaline by the addition of 10% sodium hydroxide. The alkaline solution was extracted several times with diethyl ether, and the ethereal extracts were combined, washed with water, dried, and the solvent was removed by evaporation to provide the product as a solid. The solid was dissolved in fresh diethyl ether and converted to the hydrochloride salt by the addition of hydrogen chloride. Crystallization of the salt from ethanol and diethyl ether afforded 3.7 g. of N-isopropyl-5-aminocarbonyl-5-(1,1'-biphenyl-2-yl)pentylaminium chloride. M.P. 2.5°–217° C.

Analysis calc. for $C_{21}H_{29}ClN_2O$: Theory: C, 59.88; H, 8.10; N, 7.76. Found: C, 69.95; H, 7.87; N, 7.56.

EXAMPLE 45

Formulation suitable for oral administration.

| Ingredient | Mg. |
|---|---|
| N-isopropyl-4-hydroxy-4-(1,1'-biphenyl-2-yl)butylaminium chloride | 25 |
| starch | 200 |
| sucrose | 275 |
| | 500 |

The above ingredients were thoroughly mixed with a suitable lubricant and the mixture molded into a tablet.

EXAMPLE 46

Formulation suitable for intravenous administration.

| Ingredient | |
|---|---|
| N,N-diethyl-4-aminocarbonyl-4-(5-fluoro-1,1'-biphenyl-2-yl)butylaminium chloride | 250 mg. |
| isotonic saline | 500 ml. |
| 10% aqueous glucose | 500 ml. |

The above ingredients were mixed together to form an infusion solution.

EXAMPLE 47

Formulation suitable for oral administration.

| Ingredient | Mg. |
|---|---|
| N-isopropyl-4-hydroxy-4-(1,1'-biphenyl-2-yl)butylaminium chloride | 250 |

| Ingredient | Mg. |
| --- | --- |
| starch | 300 |
| sucrose | 250 |
| | 800 |

The above ingredients are thoroughly mixed with a suitable lubricant and the mixture is molded into a tablet. Such tablet can be administered to a human at the rate of one tablet given from 1 to 3 times a day for treatment of cardiac arrhythmia.

EXAMPLE 48

Formulation suitable for intravenous administration.

| Ingredient | |
| --- | --- |
| N,N-diethyl-4-aminocarbonyl-4-(5-fluoro-1,1'-biphenyl-2-yl)butylaminium chloride | 250 mg. |
| isotonic saline | 500 ml. |
| 10% aqueous glucose | 500 ml. |

The above ingredients are mixed and the solution is infused into a subject suffering from an arrhythmia at the rate of about 1 ml. per minute until a conversion to normal sinus rhythm is effected.

We claim:

1. A compound of the formula

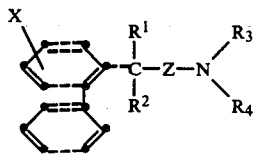

wherein:

X is hydrogen or halo;
$R^1$ is hydrogen, hydroxy, C≡N, $CONH_2$ or $COOR^5$, where $R^5$ is hydrogen or lower alkyl;
$R^2$ is hydrogen or $C_1$-$C_3$ alkyl;
Z is —$(CH_2)_n$—, or

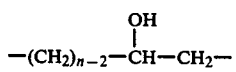

where n is 2, 3 or 4;
$R^3$ and $R^4$ independently are hydrogen, lower alkyl, lower alkenyl, phenyl alkyl, or taken together with the nitrogen to which they are attached form a cyclic ring selected from pyrrolidino, piperidino, and morpholino, and the pharmaceutically acceptable acid addition salts and quaternary ammonium salts thereof.

2. The compound of claim 1 wherein:
X is hydrogen, 5-fluoro, 5-chloro, or 5-bromo;
$R^1$ is hydrogen, hydroxy, C≡N, $CONH_2$, or COOH;
$R^2$ is hydrogen or methyl;
Z is —$CH_2CH_2$—, —$CH_2CH_2CH_2$— or

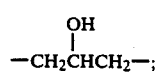

with the limitation that when X is $R^1$ is hydrogen;
$R^3$ and $R^4$ independently are hydrogen, lower alkyl, lower alkenyl, phenyl alkyl, or taken together with the nitrogen atom to which they are attached form a cyclic ring selected from pyrrolidino, piperidino and morpholino; and the pharmaceutically acceptable acid addition salts and quaternary ammonium salts thereof.

3. The compound of claim 2 wherein $R^3$ is other than hydrogen.

4. The compound of claim 3 wherein $R^2$ is hydrogen.

5. The compound of claim 4 wherein Z is —$CH_2CH_2CH_2$—.

6. The compound of claim 5 wherein X is hydrogen, fluoro or chloro.

7. The compound of claim 6 wherein $R^3$ is $C_1$-$C_4$ alkyl.

8. The compound of claim 7 wherein $R^1$ is hydroxy.

9. The compound of claim 8, said compound being N,N-dimethyl-4-hydroxy-4-[(5-fluoro-1,1'-biphenyl)-2-yl]butylamine.

10. The compound of claim 8, said compound being N-isopropyl-4-hydroxy-4-[(5-fluoro-1,1'-biphenyl)-2-yl]butylamine.

11. The compound of claim 8, said compound being N-isopropyl-4-hydroxy-4-(1,1'-biphenyl-2-yl)butylamine.

12. The compound of claim 8, said compound being N,N-diisopropyl-4-hydroxy-4-(1,1'-biphenyl-2-yl)butylamine.

13. The compound of claim 8, said compound being N-isopropyl-N-methyl-4-hydroxy-4-(1,1'-biphenyl-2-yl)butylamine.

14. The compound of claim 8, said compound being N-tert-butyl-4-hydroxy-4-[(5-fluoro-1,1'-biphenyl)-2-yl]butylamine.

15. The compound of claim 8, said compound being N,N-dimethyl-4-hydroxy-4(5-chloro-1,1'-biphenyl-2-yl)butylamine.

16. The compound of claim 7 wherein $R^1$ is C≡N.

17. The compound of claim 16, said compound being N,N-dimethyl-4-cyano-4-(1,1'-biphenyl-2-yl)butylamine.

18. The compound of claim 16, said compound being N,N-diisopropyl-4-cyano-4-(1,1'-biphenyl-2-yl)butylamine.

19. The compound of claim 16, said compound being N-benzyl-N-isopropyl-4-cyano-4-(1,1'-biphenyl-2-yl)butylamine.

20. The compound of claim 7 wherein $R^1$ is $CONH_2$.

21. The compound of claim 20, said compound being N,N-dimethyl-4-aminocarbonyl-4-(1,1'-biphenyl-2-yl)butylamine.

22. The compound of claim 20, said compound being N-isopropyl-4-aminocarbonyl-4-(1,1'-biphenyl-2-yl)butylamine.

23. The compound of claim 20, said compound being N,N-diisopropyl-4-aminocarbonyl-4-(1,1'-biphenyl-2-yl)butylamine.

24. The compound of claim 20, said compound being N-benzyl-N-isopropyl-4-aminocarbonyl-4-(1,1'-biphenyl-2-yl)butylamine.

25. The compound of claim 4 wherein Z is $$-CH_2\overset{OH}{\underset{|}{C}}HCH_2-.$$

26. The compound of claim 25 wherein $R^3$ is $C_1$-$C_4$ alkyl.

27. The compound of claim 26, said compound being N-isopropyl-2-hydroxy-4-(1,1'-biphenyl-2-yl)butylamine.

28. The compound of claim 26, said compound being N,N-diisopropyl-2-hydroxy-4-(1,1'-biphenyl-2-yl)butylamine.

29. The compound of claim 4 wherein Z is —$CH_2CH_2CH_2CH_2$—.

30. The compound of claim 29 wherein $R^1$ is hydroxy.

31. The compound of claim 29 wherein $R^1$ is $CONH_2$.

32. The compound of claim 31, said compound being N-isopropyl-5-aminocarbonyl-5-(1,1'-biphenyl-2-yl)pentylamine.

33. The compound of claim 1 as the pharmaceutically acceptable acid addition salt.

34. The compound of claim 1 as the pharmaceutically acceptable quaternary ammonium salt.

35. A pharmaceutical formulation useful in the treatment of cardiac arrhythmia comprising a compound of claim 1 in combination with a carrier therefor.

36. The formulation of claim 35 employing a compound wherein:
X is hydrogen, 5-fluoro, 5-chloro or 5-bromo;
$R^1$ is hydrogen, hydroxy, C≡N, $CONH_2$, or COOH;
$R^2$ is hydrogen or methyl; and
Z is —$CH_2CH_2$—, —$CH_2CH_2CH_2$— or $$-CH_2\overset{OH}{\underset{|}{C}}HCH_2;$$

with the limitation that when Z is $$CH_2\overset{OH}{\underset{|}{C}}HCH_2,$$

$R^1$ is hydrogen.

37. The formulation of claim 36 wherein in the active ingredient, $R^1$ is hydroxy, C≡N or $CONH_2$; $R^2$ is hydrogen and $R^3$ is $C_1$-$C_4$ alkyl.

38. The formulation of claim 37 wherein in the active ingredient, X is hydrogen, chloro or fluoro and Z is —$CH_2CH_2CH_2$.

39. The formulation of claim 35 wherein the active ingredient is a pharmaceutically acceptable acid addition salt.

40. The formulation of claim 35 wherein the active ingredient is a quaternary ammonium salt.

41. A method of treating cardiac arrhythmias comprising administering an antiarrhythmically effective amount of a compound of claim 1 to a subject suffering from an arrhythmia and in need of treatment or to a subject suspected of developing an arrhythmia.

42. The method of claim 41 employing a compound wherein:
X is hydrogen, 5-fluoro, 5-chloro or 5-bromo;
$R^1$ is hydrogen, hydroxy, C≡N, $CONH_2$ or COOH;
$R^2$ is hydrogen or methyl; and
Z is —$CH_2CH_2$—, —$CH_2CH_2CH_2$— or $$CH_2\overset{OH}{\underset{|}{C}}HCH_2;$$

with the limitation that when Z is $$-CH_2\overset{OH}{\underset{|}{C}}HCH_2-,$$

$R^1$ is hydrogen.

43. The method of claim 42 wherein in the compound administered, $R^3$ is $C_1$-$C_4$ alkyl and X is hydrogen, chloro or fluoro.

44. The method of claim 41 wherein the compound is administered in the form of a pharmaceutically acceptable acid addition salt.

45. The method of claim 41 wherein the compound is administered in the form of a quaternary ammonium salt.

* * * * *